US008153835B2

(12) United States Patent
Nakamura et al.

(10) Patent No.: US 8,153,835 B2
(45) Date of Patent: Apr. 10, 2012

(54) FULLERENE DERIVATIVES

(75) Inventors: Eiichi Nakamura, Tokyo (JP); Yutaka Matsuo, Tokyo (JP); Yu-Wu Zhong, Ithaca, NY (US); Ayako Muramatsu, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 448 days.

(21) Appl. No.: 12/281,294

(22) PCT Filed: Nov. 2, 2006

(86) PCT No.: PCT/JP2006/322409
§ 371 (c)(1),
(2), (4) Date: Oct. 29, 2008

(87) PCT Pub. No.: WO2007/102255
PCT Pub. Date: Sep. 13, 2007

(65) Prior Publication Data
US 2009/0247777 A1    Oct. 1, 2009

(30) Foreign Application Priority Data

Mar. 7, 2006  (JP) ................................. 2006-061143

(51) Int. Cl.
*C07F 7/04* (2006.01)
*C07F 7/08* (2006.01)
(52) U.S. Cl. ....................................... 556/465; 556/489
(58) Field of Classification Search .......... None
See application file for complete search history.

(56) References Cited

U.S. PATENT DOCUMENTS

2003/0139617 A1    7/2003  Nakamura et al.

FOREIGN PATENT DOCUMENTS

| JP | 10-167994 | | 6/1998 |
| JP | 11-255509 | * | 9/1999 |
| JP | 2002-241323 | * | 8/2002 |
| JP | 2003-146915 | * | 5/2003 |
| JP | 2003-146915 | | 7/2003 |
| JP | 2003-212881 | | 7/2003 |
| JP | 2004-155674 | | 6/2004 |
| JP | 2004-331848 | * | 11/2004 |

OTHER PUBLICATIONS

Matsuo et al., {Stacking of Molecules Possessing a Fullerene Apex and a Cup-Shaped Cavity Connected by a Silicon Connection, Journal of the American Chemical Society (2004), 126(2), 432-433}.*

(Continued)

*Primary Examiner* — Daniel Sullivan
*Assistant Examiner* — Jennifer C Sawyer
(74) *Attorney, Agent, or Firm* — Morgan Lewis & Bockius LLP

(57) ABSTRACT

The present invention provides a fullerene derivative represented by the following formula (1):
wherein in formula (1), $R^1$ is a substituted or unsubstituted organic group or a hydrogen atom, and wherein in formulae (2) and (3): W is a single bond, $C_1$-$C_{11}$ alkylene, $C_2$-$C_{12}$ alkenylene, or $C_2$-$C_{12}$ alkynylene, wherein any —$CH_2$— in the alkylene, alkenylene or alkynylene can be substituted with —O—, —S—, —COO—, or —OCO—; Z is an element belonging to group IVB; and $R^{21}$ to $R^{23}$ are each independently a substituted or unsubstituted $C_1$-$C_{20}$ alkyl group, a substituted or unsubstituted $C_2$-$C_{15}$ alkenyl group, or a substituted or unsubstituted $C_2$-$C_{15}$ alkynyl group.

9 Claims, 8 Drawing Sheets

OTHER PUBLICATIONS

Zhong et al, {Convergent Synthesis of a Polyfunctionalized Fullerene by Regioselective Five-Fold Addition of a Functionalized Organocopper Reagent to C60, Organic Letters (2006), 8(7), 1463-1466}.*

Sawamura, M., et. al.: "The First Pentahaptofullerence Metal Complexes", J. Am. Chem. Soc., vol. 118, pp. 12850-12851, 1996.

Sawamura, M., et al.: Stepwise Synthesis of Fullerene Cyclopentadienide $R_5C_{60}$ and Idenide $R_3C_{60}$. An Approach to Fully Unsymmetrically Substituted Derivatives:, org. Lett., vol. 2(13), pp. 1919-1921, 2000.

Sawamura, M., et al.: "Pentaorgano[60]fullerene R $_5C_{60}$. A Water Soluble Hydrocarbon Anion", Chem Lett., pp. 1098-1099, 2000.

Tschierske, C.: "Liquid Crystals Stack Up", Nature, vol. 419, pp. 681-682, 2002.

Komatsu, K., et al.: "Fullerence no yuuki kagaku", Gendai Kagaku, pp. 46-53, 2000 with its partial translation.

Martin, N., et al.: "C60-Based Electroactive Organofullerenes", Chem. Rev. 98, pp. 2527-2547, 1998.

Matsuo, Yutaka, et al.: "Stacking of Molecules Possessing a Fullerene Apex and a Cup-Shaped Cavity Connected by a Silicon Connection", Journal of the American Chemical Society, vol. 126(2), pp. 432-433, 2004.

Matsuo, Yutaka, et al.: "Ruthenium (II) Complexes of Pentamethylated [60] Fullerene. Alkyl, Alkynyl, Chloro, Isocyanide, and Phosphine Complexes", Organometallics, vol. 22(13), pp. 2554-2563, 2003.

Birkett, Paul R., et al.: "Arylation of [60] Fullerene via Electrophilic Aromatic Substitution Involving the Electrophile C60C16: Front Side Nucleophilic Substitution of Fullerenes", Journal of the Chemical Society, Perkin Transactions 2: Physical Organic Chemistry, (6), pp. 1121-1125, 1997.

Ayako Muramatsu, Interim Report Regarding Research Achievement, Nov. 17, 2005.

* cited by examiner

FULLERENE DERIVATIVES

CROSS-REFERENCE TO RELATED APPLICATIONS

The present application is a U.S. National Phase Application of International Application PCT/JP2006/322409 filed Nov. 2, 2006, which claims the benefit of Japanese Patent Application No. 2006-061143, filed Mar. 7, 2006, each of which is incorporated by reference in its entirety.

TECHNICAL FIELD

The present invention relates to fullerene derivatives.

BACKGROUND ART

Since the method for synthesizing a carbon cluster (hereinafter also referred to as "fullerene"), in which carbon atoms are arranged to form a spherical shape or a rugby ball shape, was established, fullerene has been energetically studied. As a result, many fullerene derivatives have been synthesized.

With respect to specific examples of such fullerene derivatives, methods for synthesizing a fullerene derivative, in which 5 organic groups bind to a fullerene skeleton (hereinafter also just referred to as "penta(organo)fullerene derivative"), have been reported (e.g., Japanese Laid-Open Patent Publication No. Hei 10-167994; Japanese Laid-Open Patent Publication No. Hei 11-255509; J. Am. Chem. Soc., 118 12850 (1996); Org. Lett., 2, 1919 (2000); and Chem. Lett., 1098 (2000)).

Further, since a metal-containing fullerene derivative, in which a fullerene is a ligand, has electronic properties based on characteristics of the metal, it is expected that the fullerene derivative will be successfully applied to electrochemical devices. Cyclopentadienyl metal complex of fullerene, which is derived from a penta(aryl)fullerene derivative, etc., have been reported (Japanese Laid-Open Patent Publication No. Hei 11-255509).

In terms of easiness of production of a device, increase in area of a device, etc., materials having an intermediate phase (mesophase) between a solid and a liquid attract attention as functional materials, which are excellent in charge transport characteristics and physical property of photoelectron, and which can be used in electrochemical devices, and liquid crystal-blended materials comprising a fullerene derivative, etc. have been proposed (e.g., Japanese Laid-Open Patent Publication No. 2003-146915 and Japanese Laid-Open Patent Publication No. 2004-331848). Specifically, exhibition of liquid crystallinity of a carbon cluster derivative based on a fullerene derivative having a shuttlecock-like molecular shape has been reported (Japanese Laid-Open Patent Publication No 2003-146915) Unlike general discotic-type fullerene derivatives, this shuttlecock-shaped fullerene derivative has a cup stack type lamination as a conical molecule (Nature, Vol. 4, 419, 681-(2002)). Therefore, the shuttlecock-shaped fullerene derivative has a column-shaped molecular arrangement which is stabler than discotic-type fullerene derivatives and its use as a liquid crystal material is expected.

However, since the shuttlecock-shaped fullerene derivative has a column-like structure, there are problems that temperature of transition to an isotropic phase is low and that it is difficult to perform rearrangement. Therefore, it is difficult to use the shuttlecock-shaped fullerene derivative as a liquid crystal material.

Further, though it is known that liquid crystalline fullerene-ferrocene dyads and fullerene liquid crystalline dendrimers have a layer structure, it is necessary to add a bulky group to a fullerene skeleton, and therefore it is difficult to obtain a product of interest in good yield.

DISCLOSURE OF THE INVENTION

Under the above-described circumstances, a novel fullerene derivative is desired. Specifically, for example, a fullerene derivative, which has a layer structure in the crystal state or liquid crystalline state, is desired. Moreover, for example, a fullerene derivative, which can be used in a liquid crystal material, is desired.

[1] A fullerene derivative represented by the following formula (1):

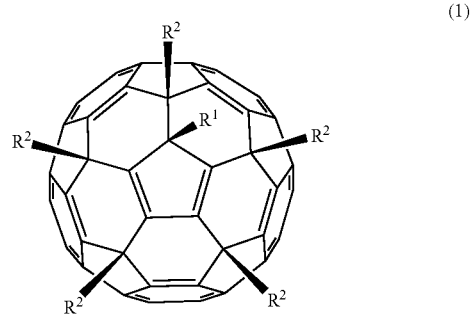

wherein:
$R^1$ is a substituted or unsubstituted organic group or a hydrogen atom; and
each $R^2$ is independently a group represented by the following formula (3) or (4),

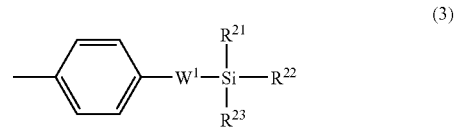

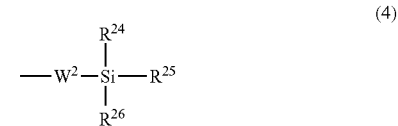

wherein:
$W^1$ is $C_2$-$C_{12}$ alkynylene, wherein any —$CH_2$— in the alkynylene is optionally substituted with —O—, —S—, —C(=O)O—, or —O—C(O)—

$W^2$ is a single bond, $C_1$-$C_{11}$ alkylene, $C_2$-$C_{12}$ alkenylene, or $C_2$-$C_{12}$ alkynylene, wherein any —$CH_2$— in the alkylene, alkenylene or alkynylene is optionally substituted with —O—, —S—, —C(=O)O—, or —O—C(O)—;

$R^{21}$ to $R^{25}$ are each independently a substituted or unsubstituted $C_1$-$C_{20}$ alkyl group, a substituted or unsubstituted $C_2$-$C_{15}$ alkenyl group, or a substituted or unsubstituted $C_2$-$C_{15}$ alkynyl group; and $R^{26}$ is a substituted or unsubstituted $C_4$-$C_{20}$ alkyl group, a substituted or unsubstituted $C_4$-$C_{15}$ alkenyl group, or a substituted or unsubstituted $C_4$-$C_{15}$ alkynyl group.

[2] The fullerene derivative according to item [1], wherein $R^1$ is a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$; in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group).

[3] The fullerene derivative according to item [1], wherein $R^1$ is a substituted or unsubstituted $C_1$-$C_{10}$ alkyl group, a substituted or unsubstituted $C_1$-$C_{10}$(alkenyl group, or a substituted or unsubstituted $C_1$-$C_{10}$ alkynyl group.

[4] The fullerene derivative according to any one of items [1] to [3], wherein $R^1$ has one or more substituents selected from the group consisting of ester group, carboxyl group, amide group, alkyne group, trimethylsilyl group, trimethylsilylethynyl group, aryl group, amino group phosphonyl group, thio group, carbonyl group, nitro group, sulfo group, imino group, halogeno group, and alkoxy group.

[5] A fullerene derivative represented by the following formula (2):

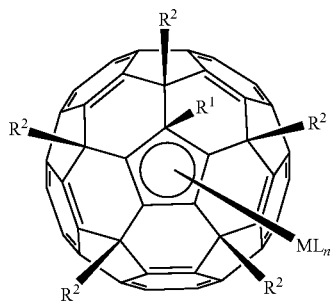

(2)

wherein:
$R^1$ is a substituted or unsubstituted organic group or a hydrogen atom; and
each $R^2$ is independently a group represented by the following formula (3) or (4),

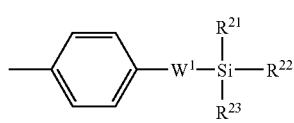

(3)

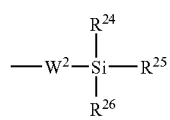

(4)

wherein:
$W^1$ is $C_2$-$C_{12}$ alkynylene, wherein any —$CH_2$— in the alkynylene is optionally substituted with —O—, —S—, —C(=O)O—, or —O—C(O)—;
$W^2$ is a single bond, $C_1$-$C_{11}$ alkylene, $C_2$-$C_{12}$ alkenylene, or $C_2$-$C_{12}$ alkynylene, wherein any —$CH_2$— in the alkylene, alkenylene or alkynylene is optionally substituted with —O—, —S—, —C(=O)O—, or —O—C(=O)—

$R^{21}$ to $R^{25}$ are each independently a substituted or unsubstituted $C_1$-$C_{20}$ alkyl group, a substituted or unsubstituted $C_2$-$C_{15}$ alkenyl group, or a substituted or unsubstituted $C_2$-$C_5$ alkynyl group; and
$R^{26}$ is a substituted or unsubstituted $C_4$-$C_{20}$ alkyl group, a substituted or unsubstituted $C_4$-$C_{15}$ alkenyl group, or a substituted or unsubstituted $C_4$-$C_{15}$ alkynyl group.

[6] The fullerene derivative according to item [5], wherein M is a transition metal.

[7] The fullerene derivative according to item [5], wherein M is a group 8-10 transition metal.

[8] The fullerene derivative according to item [5], wherein: M is Fe, Ru, or Os; n is an integer from 0 to 5; and L is a halogen atom, alkoxy group, alkyl group, alkine group or cyclopentadienyl group.

[9] The fullerene derivative according to any one of items [1] to [8], wherein $W^1$ is —C≡C—.

[10] The fullerene derivative according to any one of items [1] to [8], wherein $W^2$ is a single bond, $C_1$-$C_4$ alkylene, $C_2$-$C_4$ alkenylene, or $C_2$-$C_4$ alkynylene.

[11] The fullerene derivative according to any one of items [1] to [10], wherein $R^{21}$, $R^{22}$, $R^{24}$ and $R^{25}$ are methyl groups.

[12] The fullerene derivative according to any one of items [1] to [11], wherein the fullerene derivative in the crystal state has a layer structure.

[13] The fullerene derivative according to any one of items [1] to [11], wherein the fullerene derivative in the liquid crystalline state has a layer structure.

[14] The fullerene derivative according to any one of items [1] to [13], which has an intermediate phase.

[15] A composition, which comprises the fullerene derivative according to any one of items [1] to [14], and which has an intermediate phase.

[16] A fullerene derivative represented by the following formula (1):

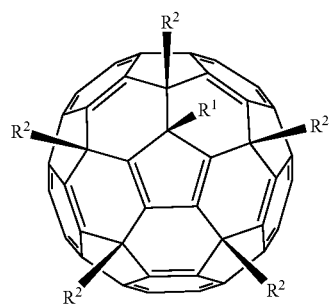

(1)

wherein:
$R^1$ is a substituted or unsubstituted organic group or a hydrogen atom; and
each $R^2$ is independently a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$ in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group), and wherein the fullerene derivative in the crystal state or liquid crystalline state has a layer structure.

[17] The fullerene derivative according to item [16], wherein $R^1$ is a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{20}$ aryl group), a substituted or unsubstituted alkylsulfonyl group (—$SO_2Y^1$: in the formula, $Y^1$ is a substituted or unsubstituted $C_1$-$C_{20}$ alkyl group), or a substituted or unsubstituted arylsulfonyl group (—$SO_2Y^4$ in the formula, $Y^4$ is a substituted or unsubstituted $C_6$-$C_{18}$ aryl group).

[18] The fullerene derivative according to item [16], wherein $R^1$ is a substituted or unsubstituted $C_1$-$C_{10}$ alkyl group, a substituted or unsubstituted $C_1$-$C_{10}$ alkenyl group, or a substituted or unsubstituted $C_1$-$C_{10}$ alkynyl group.

[19] The fullerene derivative according to any one of items [16] to [18], wherein $R^1$ has one or more substituents selected from the group consisting of ester group, carboxyl group, amide group, alkyne group, trimethylsilyl group, trimethylsilylethynyl group, aryl group, amino group, phosphonyl group, thio group, carbonyl group, nitro group, sulfo group, imino group, halogeno group, and alkoxy group.

[20] A fullerene derivative represented by the following formula (2):

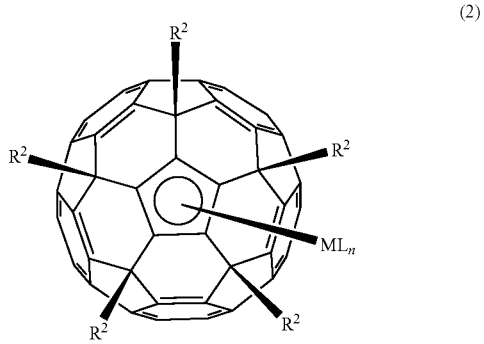

(2)

wherein:

each $R^2$ is independently a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group);

M is a metallic atom;

L is a ligand of M; and n is the number of Ls, and wherein the fullerene derivative in the crystal state or liquid crystalline state has a layer structure.

[21] The fullerene derivative according to item [20], wherein M is a transition metal.

[22] The fullerene derivative according to item [20], wherein M is a group 8-10 transition metal.

[23] The fullerene derivative according to item [20], wherein: M is Fe, Ru, or Os; n is an integer from 0 to 5; and L is a halogen atom, alkoxy group, alkyl group, alkine group or cyclopentadienyl group.

[24] The fullerene derivative according to any one of items [16] to [23], wherein $R^2$ is a substituted or unsubstituted $C_1$-$C_{10}$ alkyl group or a substituted or unsubstituted aryl group.

[25] The fullerene derivative according to any one of items [16] to [24], wherein $R^2$ has one or more substituents selected from the group consisting of ester group, carboxyl group, amide group, alkyne group, trimethylsilyl group, trimethylsilylethynyl group, aryl group, amino group, phosphonyl group, thio group, carbonyl group, nitro group, sulfo group, imino group, halogeno group, and alkoxy group.

[26] The fullerene derivative according to any one of items [16] to [24], wherein $R^2$ has one or more substituents selected from the group consisting of ester group, amide group, alkyne group, trimethylsilyl group, trimethylsilylethynyl group and aryl group.

[27] The fullerene derivative according to any one of items [16] to [26], which has an intermediate phase.

[28] A composition, which comprises the fullerene derivative according to any one of items [16] to [27], and which has an intermediate phase.

According to the preferred embodiment of the present invention, crystal of a fullerene derivative having a layer structure can be obtained in good yield. Further, in the case of the fullerene derivative according to the preferred embodiment of the present invention, a temperature of transition to an isotropic phase is high, and it is easy to perform rearrangement.

BEST MODE FOR CARRYING OUT THE INVENTION

Figure 1:
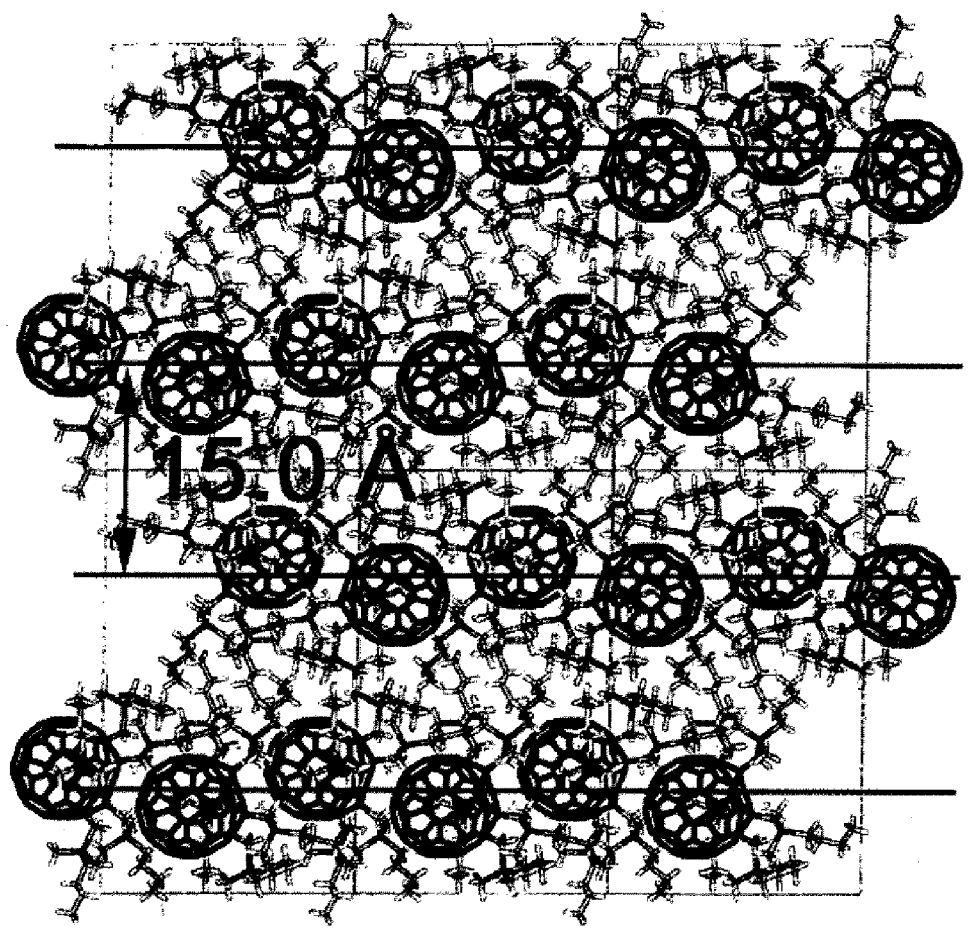
FIG. 1 shows the structure of Compound 10.

Hereinafter, the method of the present invention will be specifically described.

1. Fullerene Derivative

The fullerene derivative of the present invention is represented by the above-described formula (1) or (2). In this regard, "fullerene" is a general term for carbon clusters which are formed by arranging carbon atoms in a spherical shape or a rugby bail shape (see Gendai-Kagaku, June 2000, page 46; and Chemical Reviews 98, 2527 (1998)). Examples thereof include fullerene $C_{60}$ (so-called buckminsterfullerene), fullerene $C_{70}$, fullerene $C_{76}$, fullerene $C_{78}$, fullerene $C_{82}$, fullerene $C_{84}$, fullerene $C_{90}$, fullerene $C_{94}$, and fullerene $C_{96}$.

1.1. Fullerene Derivatives Represented by Formula (1)

In formula (1), $R^1$ is each independently a substituted or unsubstituted organic group or a hydrogen atom.

Preferably, $R^1$ is a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$— in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group). Among them, $R^1$ is preferably a substituted $C_1$-$C_{10}$ alkyl group or an unsubstituted aryl group.

Further, $R^1$ may have one or more substituents selected from the group consisting of ester group, carboxyl group, amide group, alkyne group, trimethylsilyl group, trimethylsilylethynyl group, aryl group, amino group, phosphonyl group, thio group, carbonyl group, nitro group, sulfo group, imino group, halogeno group, and alkoxy group. Among these substituents, one or more substituents selected from the group consisting of ester group, amide group, alkyne group, trimethylsilyl group, trimethylsilylethynyl group, and aryl group are preferable. Further, the number of substituents introduced into $R^1$ is preferably 0 or 1.

In formula (1), each $R^2$ is independently a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$— in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$) alkyl group), or a substituted or unsubstituted arylsulfonyl group (—$SO_2Y^4$ in the formula, $Y^4$ is a substituted or unsubstituted $C_6$-$C_{18}$ aryl group). In formula (1), preferably, at least one $R^2$ is each independently a group represented by the above-described formula (3) or (4). Moreover, among five $R^2$s in formula (1), it is preferred that as many $R^2$s as possible (in the range of 1 to 5) are each independently a group represented by the above-described formula (3) or (4). That is, among five $R^2$s in formula (1), it is preferred that as many $R^2$s as possible are groups represented by the above-described formula (3) or (4), and it is particularly preferred that five $R^2$s are groups represented by the above-described formula (3) or (4). It is most preferred that five $R^2$s are all groups represented by the above-described formula (3) or are all groups represented by the above-described formula (4).

In formula (3), $W^1$ is $C_2$-$C_{12}$ alkynylene, wherein any —$CH_2$— in the alkynylene can be substituted with —O—, —S—, —COO— or —OCO—. $W^1$ is preferably —C≡C—, since a fullerene derivative in a preferred embodiment has a layer structure in this case.

In formula (4), $R^{24}$ and $R^{25}$ are each independently a substituted or unsubstituted $C_1$-$C_{20}$ alkyl group, a substituted or unsubstituted $C_2$-$C_{15}$ alkenyl group, or a substituted or unsubstituted $C_2$-$C_{15}$ alkynyl group. Further, $R^{26}$ is preferably a substituted or unsubstituted $C_4$-$C_{20}$ alkyl group, a substituted or unsubstituted $C_4$-$C_{15}$ alkenyl group, or a substituted or unsubstituted $C_4$-$C_{15}$ alkynyl group, since a fullerene derivative in a preferred embodiment has a layer structure in this case.

The fullerene derivative represented by formula (1) preferably has a crystalline structure. More preferably, the crystalline structure is a layer structure.

When a composition only consists of the metal-containing fullerene derivative of the present invention or further comprises other substances, the metal-containing fullerene derivative represented by formula (1) may be an intermediate phase (mesophase). Herein, "intermediate phase" refers to a plastic crystal or liquid crystalline state.

In the case of carbon cluster derivatives exhibiting a thermotropic intermediate phase, an intermediate phase can be obtained by heating or cooling in a certain temperature range. In general, by heating to the state of intermediate phase and thereafter slowly cooling, a carbon cluster derivative, in which molecules are voluntarily oriented/accumulated, can be obtained. In the case of a fullerene derivative having a layer-type crystalline structure, there are advantages as follows: it is easy to perform rearrangement; an oriented state having high homogeneity can be obtained; and it is stabler than a columnar structure and the liquid crystal phase is maintained to a high temperature.

In the present specification, the hydrocarbon group of the "$C_1$-$C_{20}$ hydrocarbon group" may be a saturated or unsaturated acyclic group or a saturated or unsaturated cyclic group. When the $C_1$-$C_{20}$ hydrocarbon group is acyclic, it may be linear or branched. The "$C_1$-$C_{20}$ hydrocarbon group" includes $C_1$-$C_{20}$ alkyl group, $C_2$-$C_{20}$ alkenyl group, $C_2$-$C_{20}$ alkynyl group, $C_4$-$C_{20}$ alkyldienyl group, $C_6$-$C_{18}$ aryl group, $C_7$-$C_{20}$ alkylaryl group, $C_7$-$C_{20}$ arylalkyl group, $C_4$-$C_{20}$ cycloalkyl group, $C_4$-$C_{20}$ cycloalkenyl group, and ($C_3$-$C_{10}$ cycloalkyl) $C_1$-$C_{10}$ alkyl group.

In the present specification, the "$C_1$-$C_{20}$ alkyl group" is preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, the "$C_2$-$C_{20}$ alkenyl group" is preferably $C_2$-$C_{10}$ alkenyl group, and more preferably $C_2$-$C_6$ alkenyl group. Examples of alkenyl groups include, but are not limited to, vinyl, allyl, propenyl, isopropenyl, 2-methyl-1-propenyl, 2-methylallyl, and 2-butenyl.

In the present specification, the "$C_2$-$C_{20}$ alkynyl group" is preferably $C_2$-$C_{10}$ alkynyl group, and more preferably $C_2$-$C_6$ alkynyl group. Examples of alkynyl groups include, but are not limited to, ethynyl, propynyl, and butynyl.

In the present specification, the "$C_4$-$C_{20}$ alkyldienyl group" is preferably $C_4$-$C_{10}$ alkyldienyl group, and more preferably $C_4$-$C_6$ alkyldienyl group. Examples of alkyldienyl groups include, but are not limited to, 1,3-butadienyl.

In the present specification, the "$C_6$-$C_{18}$ aryl group" is preferably $C_6$-$C_{10}$ aryl group. Examples of aryl groups include, but are not limited to, phenyl, 1-naphthyl, 2-naphthyl, indenyl, biphenylyl, anthryl, and phenanthryl.

In the present specification, the "$C_7$-$C_{20}$ alkylaryl group" is preferably $C_7$-$C_{12}$ alkylaryl group. Examples of alkylaryl groups include, but are not limited to, o-tolyl, m-tolyl, p-tolyl, 2,3-xylyl, 2,4-xylyl, 2,5-xylyl, o-cumenyl, m-cumenyl, p-cumenyl, and mesityl.

In the present specification, the "($C_7$-$C_{20}$ arylalkyl group" is preferably $C_7$-$C_{12}$ arylalkyl group. Examples of arylalkyl groups include, but are not limited to, benzyl, phenethyl, diphenylmethyl, triphenyl methyl, 1-naphthylmethyl, 2-naphthylmethyl, 2,2-diphenylethyl, 3-phenylpropyl, 4-phenylbutyl, and 5-phenylpentyl.

In the present specification, the "$C_{4-20}$ cycloalkyl group" is preferably $C_4$-$C_{10}$ cycloalkyl group. Examples of cycloalkyl groups include, but are not limited to, cyclopropyl, cyclobutyl, cyclopentyl, and cyclohexyl.

In the present specification, the "$C_4$-$C_{20}$ cycloalkenyl group" is preferably $C_4$-$C_{10}$ cycloalkenyl group. Examples of cycloalkenyl groups include, but are not limited to, cyclopropenyl, cyclobutenyl, cyclopentenyl, and cyclohexenyl.

In the present specification, the "$C_1$-$C_{20}$ alkoxy group" is preferably $C_1$-$C_{10}$ alkoxy group, and more preferably $C_1$-$C_6$ alkoxy group. Examples of alkoxy groups include, but are not limited to, methoxy, ethoxy, propoxy, butoxy, and pentyloxy In the present specification, the "$C_6$-$C_{20}$ aloxy group" is preferably $C_6$-$C_{10}$ aryloxy group. Examples of aryloxy groups include, but are not limited to, phenyloxy, naphthyloxy, and biphenyloxy.

In the present specification, in "alkylthio group (—$SY^1$: in the formula, $Y^1$ is a substituted or unsubstituted $C_1$-$C_{20}$ alkyl group)" and "alkylsulfonyl group (—$SO_2Y^3$: in the formula, $Y^3$ is a substituted or unsubstituted $C_1$-$C_{20}$ alkyl group)", $Y^1$ and $Y^3$ are preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, in "arylthio group (—$SY^2$: in the formula, $Y^2$ is a substituted or unsubstituted $C_6$-$C_{18}$ aryl group)" and "arylsulfonyl group (—$SO_2Y^4$: in the formula, $Y^4$ is a substituted or unsubstituted $C_6$-$C_{18}$ aryl group)" $Y^2$ and $Y^4$ are preferably $C_6$-$C_{10}$ aryl group. Examples of aryl groups include, but are not limited to, phenyl, 1-naphthyl, 2-naphthyl, indenyl, biphenylyl, anthryl, and phenanthryl.

"$C_1$-$C_{20}$ hydrocarbon group," "$C_1$-$C_{20}$ alkoxy group," "$C_6$-$C_{20}$ aryloxy group," "amino group," "silyl group," "alkylthio group," "arylthio group," "alkylsulfonyl group," and "arylsulfonyl group" may be substituted. Examples of substituents in these cases include ester group, carboxyl group, amide group, alkyne group, trimethylsilyl group, amino group, phosphonyl group, thio group, carbonyl group, nitro group, sulfo group, imino group, halogeno group, and alkoxy group. In these cases, one or more substituents may be introduced into replaceable positions, and preferably, 1 to 4 substituents are introduced. When the number of substituents is 2 or more, the substituents may be the same or different.

In the present specification, examples of "substituted or unsubstituted amino group" include, but are not limited to, amino, dimethylamino, methylamino, methylphenylamino, and phenylamino.

In the present specification, examples of "substituted or unsubstituted silyl group" include, but are not limited to, dimethylsilyl diethylsilyl, trimethylsilyl, triethylsilyl, trimethoxysilyl, triethoxysilyl, diphenylmethylsilyl, triphenylsilyl, triphenoxysilyl, dimethylmethoxysilyl, dimethylphenoxysilyl, and methylmethoxyphenyl.

The fullerene derivative represented by formula (1) preferably has a crystalline structure. More preferably, the crystalline structure is a layer structure. Further, the fulerene derivative represented by formula (1) may have a layer structure in liquid crystal.

1.2. Fullerene Derivatives Resented by Formula (2)

In formula (2), each $R^2$ is independently a substituted or unsubstituted organic group or a hydrogen atom; M is a metallic atom; L is a ligand of M; and n is the number of Ls.

M is not particularly limited as long as it is a metallic atom, and it may be a typical metal or transition metal. Specific examples of M include: typical metals such as Li, K, Na, Mg, and Al; and transition metals such as Ti, Zr, V, Cr, Mo, W, Mn, Re, Fe, Ru, Os, Rh, Ir, Ni, Pd, Pt, Cu, and Zn. When using the obtained fullerene derivative in an electronic material, M is preferably a transition metal since an electronic nature based on redox behavior peculiar to metal is provided to the fullerene skeleton. Among transition metals, group 8-10 transition metals such as Fe, Ru, Os, Rh, Ir, Ni, Pd and Pt are preferred, and group 8 transition metals such as Fe, Ru and Os are more preferred.

n is the number of Ls (ligands of M), and it is not particularly limited as long as it is less than or equal to an integer which can be the number of ligands of M and is more than 0. Preferably, n is an integer from 0 to 5. When the number of Ls is 2 or more, the ligands (Ls) may be the same or different.

Further, L is preferably a hydrogen atom; a halogen atom such as Cl, Br and I; an alkoxy group such as methoxy group and ethoxy group; an alkyl group such as methyl group and ethyl group; a carbonyl group; an alkyne group; or a cyclopentadienyl group.

Moreover, among five $R^2$s in formula (2) it is preferred that as many $R^2$s as possible (in the range of 1 to 5) are each independently a group represented by the above-described formula (3) or (4). That is, among five $R^2$s in formula (1), it is preferred that as many $R^2$s as possible are groups represented by the above-described formula (3) or (4).

Note that $R^1$ in formula (2) is as described above.

The fullerene derivative represented by formula (2) preferably has a crystalline structure. More preferably, the crystalline structure is a layer structure. Further, the fullerene derivative represented by formula (2) may have a layer structure in liquid crystal.

When a composition only consists of the metal-containing fullerene derivative of the present invention or further comprises other substances, the metal-containing fullerene derivative represented by formula (2) may be an intermediate phase.

In the case of carbon cluster derivatives exhibiting a thermotropic intermediate phase, an intermediate phase can be obtained by heating or cooling in a certain temperature range. In general, by heating to the state of intermediate phase and thereafter slowly cooling, a carbon cluster derivative, in which molecules are voluntarily oriented/accumulated, can be obtained. In the case of a fullerene derivative having a layer-type crystalline structure, there are advantages as follows: it is easy to perform rearrangement; an oriented state having high homogeneity can be obtained; and it is stabler than a columnar structure and the liquid crystal phase is maintained to a high temperature.

2. Method for Producing the Fullerene Derivative of the Present Invention

The fullerene derivative represented by formula (1) can be produced using, for example, the methods described in Japanese Laid-Open Patent Publication Nos. 10-167994, 11-255509 and 2002-241323 and methods according thereto.

For example, an organocopper reagent such as CuBr.S $(CH_3)_2$ is mixed with an inert solvent such as toluene, tetrahydrofuran, dichlorobenzene and a mixture thereof, an additive such as dimethylimidazolidinone and a Grignard reagent are added thereto, and the obtained mixture is stirred. After that, with the reaction system, fullerene dissolved in an organic solvent is mixed to produce the fullerene derivative of the present invention. A synthesis reaction of the fullerene derivative of the present invention can be terminated by adding an aqueous solution of ammonium chloride or the like to the reaction system.

The reaction is preferably performed under ordinary pressure at a temperature of −70° C. to 70° C., and more preferably at a temperature of −50° C. to 50° C.

Reaction time depends on a solvent used, temperature, etc. In general, the reaction is performed for about several minutes to 5 hours, and preferably for about 10 minutes to 4 hours.

A method for isolating the fullerene derivative from the reaction system is not particularly limited. For example, isolation is performed by passing a reaction solution through a silica gel column to remove by-products such as inorganic substances. Depending on the necessity, isolated substances may be further purified by HPLC, general column chromatography or the like to improve purity of the fullerene derivative.

The fullerene derivative represented by formula (2) can be produced using, for example, the methods described in Japanese Laid-Open Patent Publication No. 10-167994, etc. or methods according thereto. Specifically, it can be obtained by reacting the fullerene derivative represented by formula (1) with metal alkoxide.

As metal alkoxide to be used in the production of the metal complex of the present invention, alkali metals such as Li and K; transition metals such as Tl, Cu and Ru; and metal alkoxide comprising lanthanoid metal such as Sm(III) can be used. Further, as an alkoxy group that constitutes metal alkoxide, for example, lower alkoxy groups such as $C_1$-$C_6$ alkoxy group can be used. Examples thereof include methoxy group, ethoxy group, n-propoxy group, isopropoxy group, n-butoxy group, sec-butoxy group, tert-butoxy group, and neopentoxy group. As metal alkoxide, for example, lithium tert-butoxide, potassium tert-butoxide, thallium ethoxide, copper tert-butoxide and the like can be used.

For example, a reaction between the fullerene derivative represented by formula (1) and metal alkoxide can be generally performed in an inert solvent at a temperature of about −78° C. to room temperature using metal alkoxide in an amount of about 0.5 to 1.5 equivalent, preferably in an amount of about 1.0 equivalent of the carbon cluster derivative (III). The type of solvent is not particularly limited as long as it is inert at the time of reaction. Examples of solvents include tetrahydrofuran and toluene. When another ligand is coordinated to a metal atom, a reaction can be performed in the presence of a phosphorous compound or the like. For example, in the case of using Cu(I) tert-butoxide, if a phosphine compound such as triethyl phosphine is added, a metal complex, in which the phosphine compound is coordinated/bonded to a metal atom, can be obtained.

3. Uses of the Fullerene Derivative of the Present Invention

The fullerene derivative of the preferred embodiment of the present invention has various characteristics such as magnetic, electrical, optical, photochemical and electrochemical characteristics, and orientation/accumulation of molecules attributed to an intermediate phase and the like allow utilization of the fullerene derivative in various indicating devices, optical devices, photoelectric conversion devices, etc.

The fullerene derivative of the preferred embodiment of the present invention is very useful as a liquid crystal material since the temperature of transition to the intermediate phase is high and it is easy to perform rearrangement.

Moreover, when using the carbon cluster derivative of the preferred embodiment of the present invention in various devices, it can be used in a state in which molecular orientation attributed to the intermediate phase is utilized, and it can also be used in the solid state after molecular orientation attributed to the intermediate phase is given thereto.

The metal-containing fullerene derivative of the preferred embodiment of the present invention may have a metal atom, and natures peculiar to the metal atom are given thereto. As a result, for example, the metal-containing fullerene derivative can be utilized in devices of electronic materials and the like in which electrical behavior based on redox behavior of the metal atom in addition to redox behavior derived from the fullerene skeleton is utilized.

EXAMPLES

Hereinafter the present invention will be described in more detail based on Examples. However, the present invention is not limited thereby Example 1

Compound Represented by the Following Formula (10)

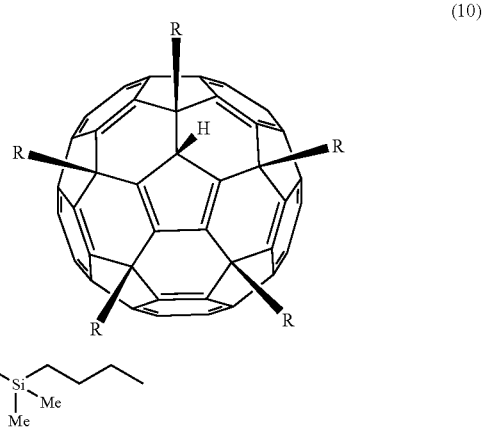

Copper bromide-dimethylsulfide complex (1.03 g, 5.05 mmol) was suspended in 20 mL of tetrahydrofuran. The mixture was maintained at 0° C., and dimethylimidazolidinone (0.54 mL, 4.46 mmol) and $BuMe_2SiCH_2MgCl$ (1.03M THF solution, 4.33 mL, 4.46 mmol) were added to the mixture, and the obtained mixture was stirred. After stirring for 5 minutes, 1,2-dichlorobenzene solution (25 mL) of $C_{60}$ (200 mg, 0.28 mmol) was added to the mixture and heated to 25° C. After stirring for 1 hour, 0.25 mL of saturated ammonium chloride solution was added to the mixture. The reaction mixture was diluted with 150 mL of toluene. Toluene was used as a developing solvent, and the mixture was passed through a short-pass silica get column to remove by-products such as copper salt, etc. The solvent was distilled away until the amount of the remaining solvent became about 5 mL. 300 mL of methanol was added to the remaining solvent to perform reprecipitation, and a compound represented by formula (10) having the purity of about 95% (hereinafter referred to as "Compound 10", etc.) was obtained. Note that "Me" represents methyl in the present specification. The isolated yield was 87% (379 mg).

NMR and UV data of the obtained Compound 10 were as follows:

$^1$H NMR (500 Hz, CDCl3): δ 0.04 (s, 6H), 0.09-0.11 (overlapping m, 24H), 0.58-0.64 (m, 10H), 0.80-0.84 (m, 15H), 1.25-1.30 (m, 20H), 1.84-2.14 (m, 10H), 4.64 (s, 1H); $^{13}$C NMR (CDCl3): δ −1.20, −1.16, 13.68, 13.72, 16.23, 16.27, 25.95, 26.01, 26.04, 26.42, 26.45, 29.52, 29.95, 29.83, 52.86, 53.21, 54.79, 63.25, 142.34, 143.14, 143.22, 143.40, 143.64, 144.75, 144.98, 145.16, 145.49, 145.97, 146.24, 146.64, 146.87, 146.93, 147.50, 147.76, 147.78, 147.93, 148.05, 148.42, 148.45, 148.59, 149.80, 154.04, 154.30, 154.45, 157.59

USV-vis (hexane), $\lambda_{max}$ 395, 356, 348, 262, 241, 212.

Compound 10 was red powder at room temperature. The compound in the solid state was stable in air at room temperature.

By slowly diffusing methanol in chloroform solution of Compound 10, red single crystal suitable for X-ray crystal structure analysis was successfully obtained. Further, crystallographic data of crystal of Compound 10 were as follows:

Crystalline system: monoclinic, Space group: P21/c

| | |
|---|---|
| a, Å | 14.4090(7) |
| b, Å | 17.2910(8) |
| c, Å | 30.0080(12) |
| α, deg | 90.00 |
| β, deg | 101.757(3) |
| γ, deg | 90.00 |
| Volume V, Å3 | 7319.5(6) |
| Number of molecules in unit cell Z, | 4 |
| Temperature, K | 153(2) |
| Crystal size, mm | 0.3 × 0.3 × 0.3 |
| Number of independent reflections | 14605 |
| Number of parameters | |
| R1, wR2 (all data) | 0.082, 0.135 |
| R, Rw (I > 2.0s(I)) | 0.058, 0.132 |
| GOF on F2 | 1.158 |

X-ray structure analysis of crystal of Compound 10 was performed, and the structure was as shown in FIG. 1. It was confirmed from FIG. 1 that Compound 10 has a layer structure in its crystalline state.

When a fullerene derivative has an intermediate phase, it is generally confirmed by observing transition from a crystal phase to the intermediate phase and transition from the intermediate phase to an isotropic phase (liquid phase) by measurement of DSC (differential scanning calorimetry). Therefore, crystal of Compound 10 was subjected to measurement of DSC, and measurement results were as shown in FIG. 2.

Figure 2:
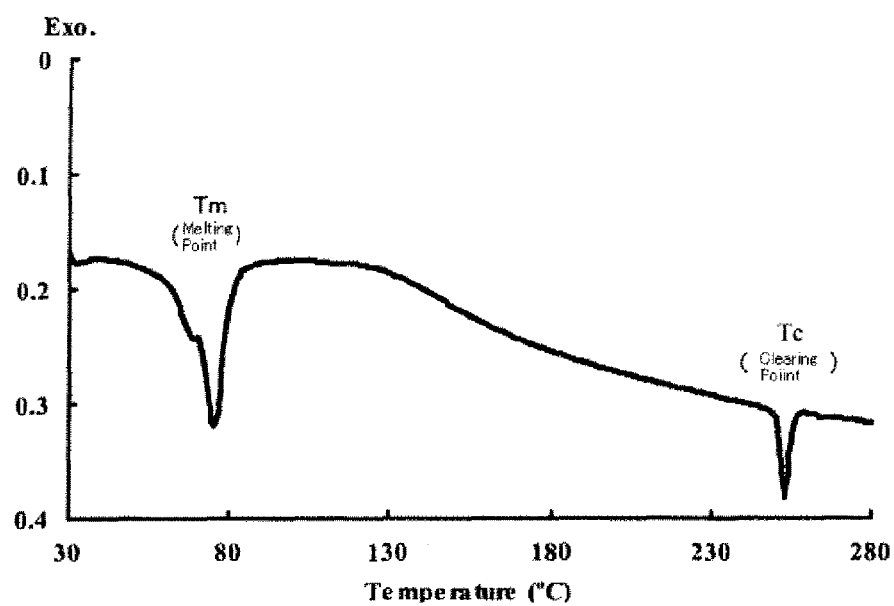
FIG. 2 shows DSC measurement result of crystal of Compound 10.

Regarding the derivative of Compound 10, it was confirmed from FIG. 2 that Tc (clearing point) is 254° C., Tm (melting point) is 75° C., and an intermediate phase is exhibited at a temperature of 75° C. to 254° C.

Further, when Compound 10 was subjected to X-ray diffraction measurement at 200° C., crystallographic data thereof were as follows:

| | |
|---|---|
| a, Å | 27.68 |
| b, Å | 21.00 |
| c, Å | 15.44 |
| α, deg | 90.00 |
| β, deg | 90.00 |
| γ, deg | 90.00 |
| Temperature, K | 473 |

Figure 3:
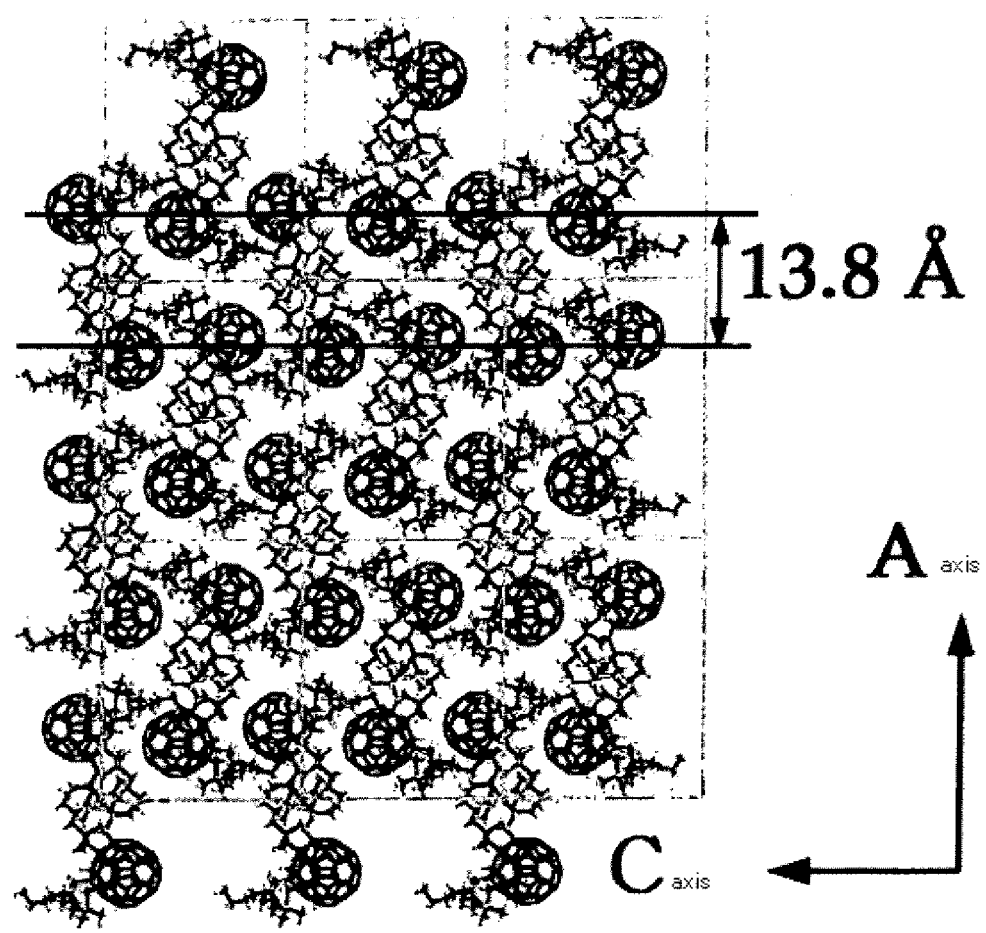
FIG. 3 shows X-ray structure analysis of Compound 10.

When Compound 10 was subjected to X-ray structure analysis at 200° C., the structure was as shown in FIG. 3. It was confirmed from the data and FIG. 3 that Compound 10 has a layer structure in its liquid crystalline state.

Example 2

Compound Represented by the Following Formula (10A)

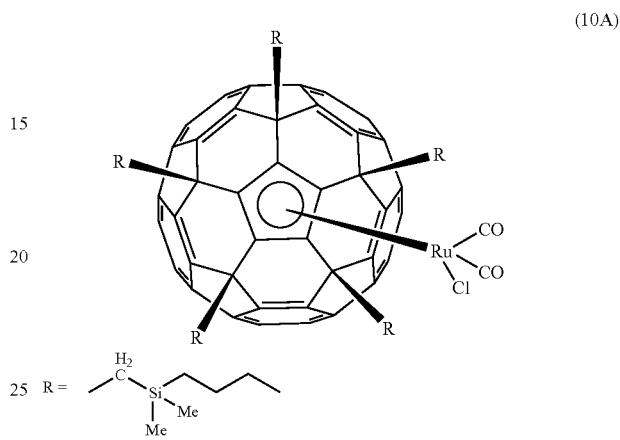

Potassium t-butoxide/THF solution (1M, 0.26 mL, 0.26 mmol) was added to tetrahydrofuran (40 mL) solution of Compound 10 (200 mg) at 25° C. After stirring for 15 minutes, [RuCl$_2$(CO)$_3$]$_2$ was added to the mixture. The reaction mixture was diluted with toluene and passed through a short-pass silica gel column, and thereafter the solution was distilled away. The solid was dissolved in carbon disulfide, and silica gel column chromatography was performed using a mixed solvent of carbon disulfide and hexane to obtain red microcrystal of Compound 10A (55 mg, 0.032 mmol, Isolated yields 25%).

NMR and UV data of the obtained Compound 10A were as follows:

$^1$H NMR (500 Hz, CDCl3): δ 0.04 (s, 30H), 0.58 (t, J=8.0 Hz, 10H), 0.80 (t, J=700 Hz, 15H), 1.24-1.26 (m, 20H), 2.17 (s, 10H); $^{13}$C NMR (CDCl3): δ −1.33, 13.65, 16.03, 25.84, 26.31, 34.76, 52.99, 115.00, 143.07, 144.03, 147.24, 148.19, 148.66, 152.11, 196.93

UV-vis (hexane) $\lambda_{max}$ 391, 356, 260, 213.

Compound 10A was red powder at room temperature. The compound in the solid state was stable in air at room temperature.

By slowly diffusing methanol in chloroform solution of Compound 10A, red single crystal suitable for X-ray crystal structure analysis was successfully obtained. Further, crystallographic data of crystal of Compound 10A were as follows:

Crystalline System: Triclinic, Space Group: P-1

| | |
|---|---|
| a, Å | 14.3750(7) |
| b, Å | 14.5870(9) |
| c, Å | 19.4600(12) |
| α, deg | 96.350(3) |
| β, deg | 101.761(3) |
| γ, deg | 107.106(3) |
| Volume V, Å3 | 3754.2(4) |
| Number of molecules in unit cell Z, | 2 |
| Temperature, K | 153(2) |

| | |
|---|---|
| Crystal size, mm | 0.3 × 0.3 × 0.3 |
| Number of independent reflections | 13385 |
| Number of parameters | 960 |
| R1, wR2 (all data) | 0.0827, 0.1916 |
| R, Rw (I > 2.0s(I)) | 0.0735, 0. 0.2077 |
| GOF on F2 | 1.045 |

Figure 4:
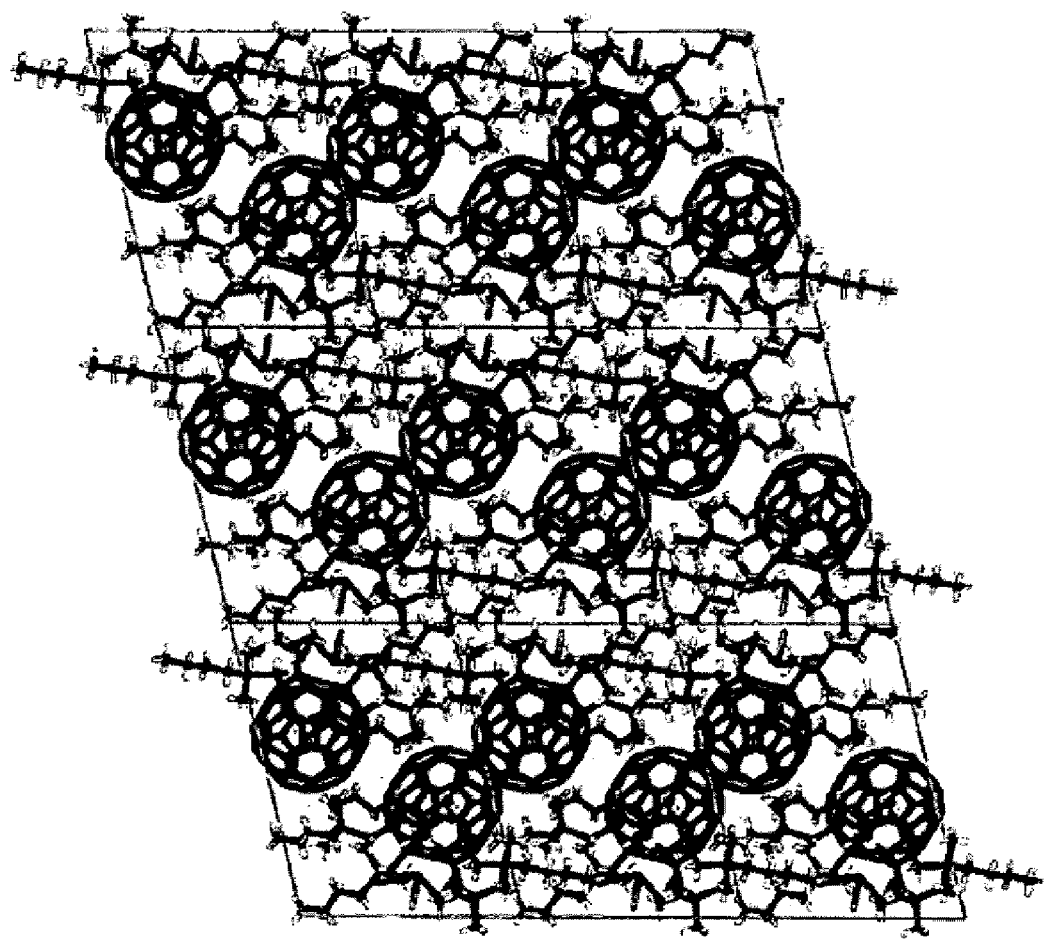
FIG. 4 shows the structure of Compound 10A.

X-ray structure analysis of crystal of Compound 10A was performed, and the structure was as shown in FIG. 4. It was confirmed from FIG. 3 that Compound 10A has a layer structure in its crystalline state.

Example 3

Compound Represented by the Following Formula (11)

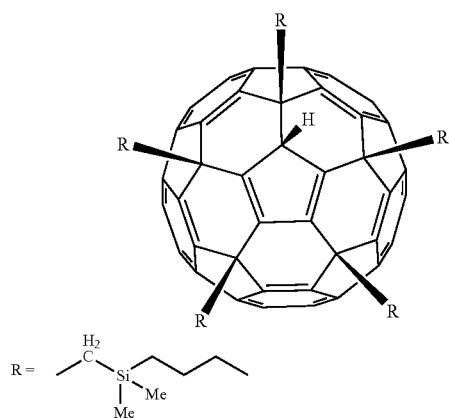

(11)

Copper bromide-dimethylsulfide complex (1.03 g, 5.05 mmol) was suspended in 20 mL of tetrahydrofuran. The mixture was maintained at 0° C., and dimethylimidazolidinone (0.54 mL, 4.46 mmol) and $BuMe_2SiCH_2MgCl$ (0.82M THF solution, 5.4 n 4.46 mmol) were added to the mixture, and the obtained mixture was stirred. After stirring for 5 minutes, 1,2-dichlorobenzene solution (25 mL) of $C_{60}$ (200 mg, 0.28 mmol) was added to the mixture and heated to 25° C. After stirring for 1 hour, 0.25 mL of saturated ammonium chloride solution was added to the mixture. The reaction mixture was diluted with 150 mL of toluene. Toluene was used as a developing solvent, and the mixture was passed through a short-pass silica gel column to remove by-products such as copper salt, etc. The solvent was distilled away until the amount of the remaining solvent became about 5 mL. 300 mL of methanol was added to the remaining solvent to perform reprecipitation, and Compound 11 having the purity of about 95% was obtained. The isolated yield was 84% (350 mg).

NMR and UV data of the obtained Compound 11 were as follows:

$^1H$ NMR (500 Hz, $CDCl_3$): δ 0.03 (s, 6H), 0.04-0.1 (overlapping m, 24H), 0.53-0.62 (m, 10H), 0.82-0.85 (m, 15H), 1.20-1.31 (m, 40H), 1.85-2.15 (m, 10H), 4.65 (s, 1H); TlC NMR (CDCl3): δ −1.20, −1.15, 14.15, 16.57, 16.61, 22.61, 23.78, 23.81, 23.84, 29.55, 29.96, 31.49, 31.53, 31.55, 33.20, 33.24, 36.84, 52.87, 53.21, 54.79, 63.26, 142.36, 143.15, 143.23, 143.41, 143.65, 144.26, 144.99, 145.17, 145.49, 145.98, 146.25, 146.64, 146.88, 146.93, 147.49, 147.76, 147.80, 147.94, 148.05, 148.42, 148.45, 148.59, 149.82, 154.03, 154.32, 154.47, 157.62

UV-vis (hexane) $λ_{max}$ 395, 356, 348, 262, 241, 211.

Compound 11 was red fluid with high viscosity at room temperature. The compound in the solid state was stable in air at room temperature.

Moreover, optical texture was observed using a polarization microscope, and the presence of intermediate phase in Compound 11 was confirmed. The intermediate phase was maintained at temperatures of up to 180° C. When Compound 11 was annealed at 180° C. for 3 hours, batonnet texture, which is often found in a smectic phase, was observed by the polarization microscope.

Moreover, as in the case of Example 1, it was confirmed from data of X-ray structure analysis that Compound 11 has a layer structure in its crystalline state.

Example 4

Compound Represented by the Following Formula (11A)

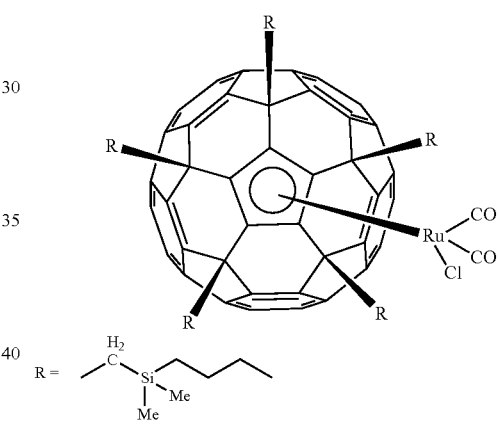

(11A)

Potassium t-butoxide/THF solution (1M, 0.26 mL, 0.26 mmol) was added to tetrahydrofuran (40 mL) solution of Compound 11 (200 mg) at 25° C. After stirring for 15 minutes, $[RuCl_2(CO)_3]_2$ (136 mg) was added to the mixture. The reaction mixture was diluted with toluene and passed through a short-pass silica gel column, and thereafter the solution was distilled away. The solid was dissolved in carbon disulfide, and silica gel column chromatography was performed using a mixed solvent of carbon disulfide and hexane to obtain Compound 11A (50.0 mg-0.0294 mmol, 23%).

NMR and UV data of the obtained Compound 11A were as follows:

$^1H$ NMR (500 Hz, $CDCl_3$): δ 0.046 (s, 30H), 0.59 (t, J=8.0 Hz, 10H), 0.85 (t, J=7.0 Hz, 15H), 1.19-1.57 (m, 40H), 2.18 (s, 10H); $^{13}C$ NMR ($CDCl_3$): δ −1.32, 14, 13, 16.37, 22.57, 23.65, 31.44, 33.10, 34, 77, 52.98, 114.99, 143.07, 144.03, 147.24, 148.18, 148.66, 152.11, 196.94

UV-vis (hexane) $λ_{max}$ 393, 356, 260, 213.

Compound 11A was fluid with high viscosity at room temperature. Optical texture, which indicates the presence of intermediate phase, was observed by a polarization microscope.

Moreover, as in the case of Example 2, when X-ray structure analysis was performed, it was confirmed from data of the structure analysis that Compound 11A has a layer structure in its crystalline state.

Example 5

Compound Represented by the Following Formula (12)

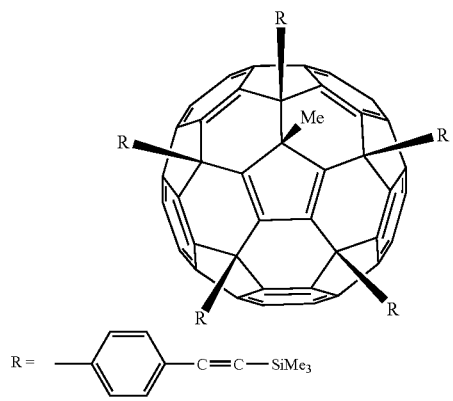

THF solution (8 mL) of (4-bromophenylethynyl)trimethylsilane (607 mg, 2.4 mL) was added dropwise to THF suspension of magnesium turnings (60 mg, 2.5 mmol). After the mixture was stirred at room temperature for 3 hours, copper bromide-dimethylsulfide complex (512 mg, 2.5 mmol) was added to the mixture to prepare an organocopper reagent. 10 minutes later, 1,2-dichlorobenzene solution (10 mL) of $C_{60}$ (144 mg, 0.2 mmol) was added thereto at once. After stirring at room temperature for 2 hours, methyl iodide (1.24 mL, 20 mmol) was added to the mixture. After stirring at room temperature for 3 hours, the reaction was terminated by the addition of saturated ammonium chloride solution. The mixture was diluted with toluene, and copper salt was removed by means of a short-pass silica gel column. The obtained filtrate was concentrated to obtain Compound 12 by means of flash column chromatography. (290 mg isolated yield: 91).

NMR data of the obtained Compound 12 were as follows:
$^1H$ NMR (CDCl$_3$): δ 0.21 (s, 9H, SiMe$_3$), 0.28 (s, 18H, SiMe$_3$), 0.30 (s, 18H, SiMe$_3$), 1.36 (s, 3H, C$_{60}$Me), 7.07 (d, J=8.00 Hz, 2H, ArH), 7.20 (d, J=8.00 Hz, 2H, ArH), 7.44 (d, J=8.00 Hz, 4H, ArH), 7.46 (d, J=8.00 Hz, 4H, ArH), 7.60 (d, J=8.00 Hz, 4H, ArH), 7.71 (d, J=8.00 Hz, 4H, ArH). $^{13}C$ NMR (CDCl$_3$): δ −0.17 (3C, SiMe$_3$), −0.06 (6C, 2SiMe$_3$), −0.02 (6C, 2SiMe$_3$), 34.35 (C$_{60}$Me), 57.95 (2C, 2C$_{60}$(C$_\alpha$)), 60.81 (2C, 2C$_{60}$(C$_\alpha$)), 62.22 (1C, C$_{60}$(C$_\alpha$)), 62.33 (1C, C$_{60}$(CMe)), 95.35 (1C, C≡CSi), 95.45 (2C, 2C≡CSi), 95.47 (2C, 2C≡CSi), 104.07 (1C, C≡CSi), 104.36 (2C, 2C≡CSi), 104.51 (2C, 2C≡CSi), 122.04 (1C, Ar), 122.79 (2C, Ar), 122.95 (2C, Ar), 127.92 (4C, Ar), 128.46 (4C, Ar), 129.54 (2C, Ar), 131.78 (2C, Ar), 132.34 (4C, Ar), 132.62 (4C, Ar), 137.93, 139.58, 142.44, 142.48, 143.50, 143.66, 143.92, 144.12, 144.30, 144.35, 144.45, 144.61, 145.25, 145.47, 147.10, 147.28, 147.30, 147.82, 148.19, 148.26, 148.37, 148.47, 148.71, 148.75, 148.82, 151.31, 152.37, 156.61, 160.64.

Compound 12 was orange powder at room temperature. The compound in the solid state was stable in air at room temperature.

By slowly diffusing methanol in chloroform solution of Compound 12, red single crystal suitable for X-ray crystal structure analysis was successfully obtained. Further, crystallographic data of crystal of Compound 12 were as follows:
Crystalline System: Triclinic, Space Group: P-1

| | |
|---|---|
| a, Å | 14.449 |
| b, Å | 17.506 |
| c, Å | 23.235 |
| α, deg | 103.57 |
| β, deg | 100.73 |
| γ, deg | 105.18 |
| Volume V, Å3 | 5318 |
| Number of molecules in unit cell Z, | 2 |
| Temperature, K | 153(2) |
| Crystal size, mm | 0.68 × 0.32 × 0.12 |
| Number of independent reflections | 16452 |
| Number of parameters | 1135 |
| R1, wR2 (all data) | 0.2962, 0.4836 |
| R, Rw (I > 2.0s(I)) | 0.1777, 0.4183 |
| GOF on P2 | 1.304 |

Figure 5:
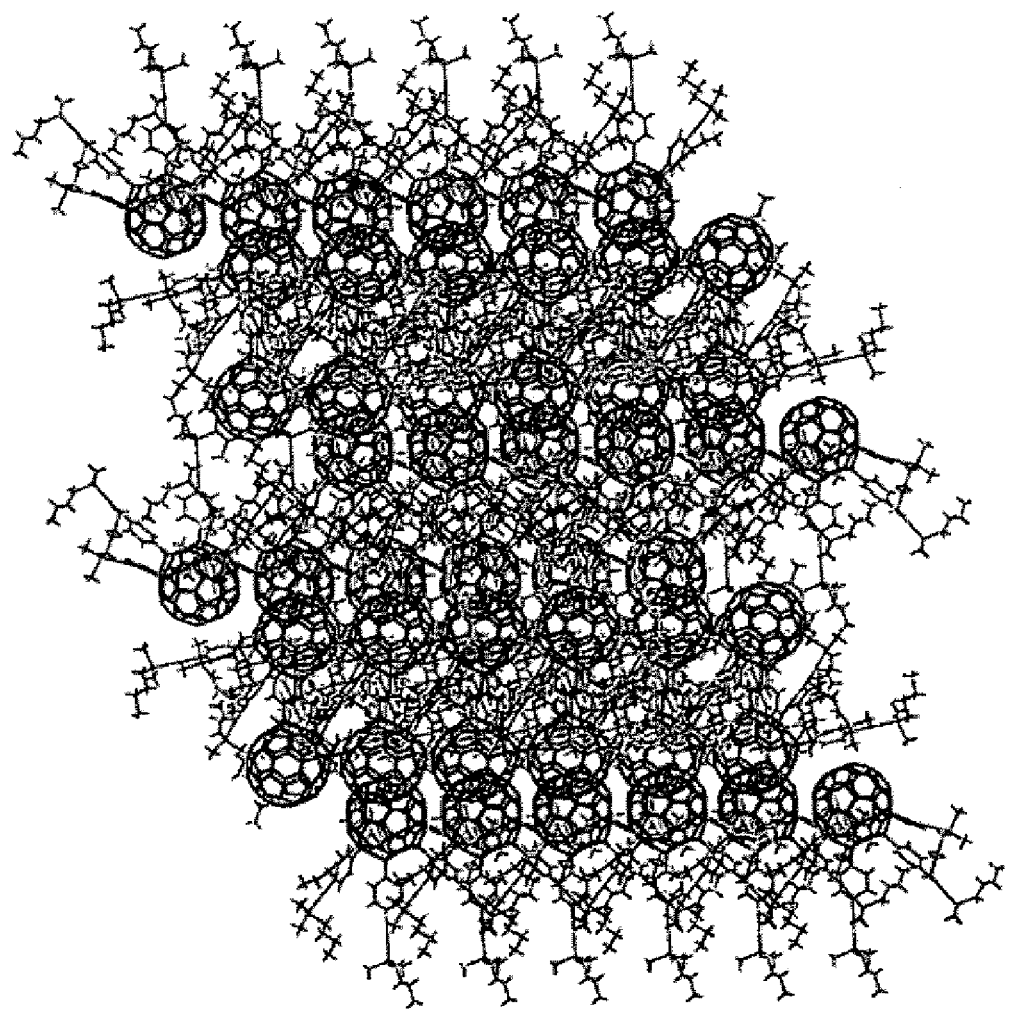
FIG. 5 shows the structure of Compound 12.

When Compound 12 was subjected to X-ray structure analysis, the structure was as shown in FIG. 5. It was confirmed from FIG. 5 that Compound 12 has a layer structure in its crystalline state.

Example 6

Compound Represented by the Following Formula (13)

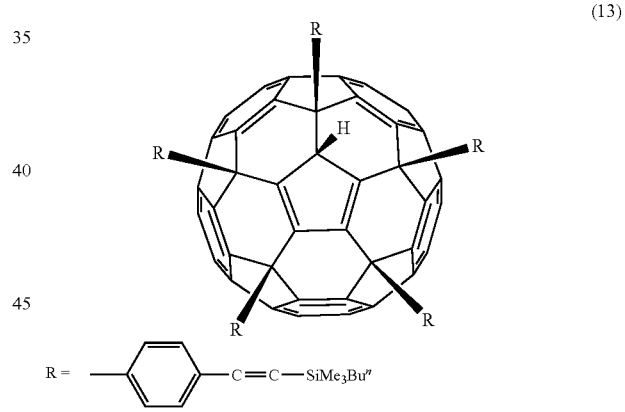

i-propylmagnesiumbromide (0.67 M/THF solution, 3.10 mL, 2.1 mmol) was added dropwise to THF solution (15 mL) of 1-bromo-4-ethynylbenzene (382 mg, 2.0 mmol) at 0° C. After the mixture was stirred for 20 minutes, an ice water bath was removed. After stirring at room temperature for 10 minutes, n-butyldimethylsilyl chloride (0.69 mL, 4.0 mmol) was added to the mixture. After stirring for 2 hours, the reaction was terminated by the addition of saturated ammonium chloride solution (5 mL). The reaction mixture was extracted with ethyl acetate, and it was concentrated and thereafter purified by means of flash column chromatography to obtain (4-bromophenylethynyl)-n-butyldimethylsilane (530 mg, isolated yield: 90%).

THF solution (4 mL) of (4-bromophenylethynyl)-n-butylethynylsilane obtained (295 mg, 1.0 mmol) was added dropwise to THF suspension (2 mL) of magnesium turnings (26 mg, 1.1 mmol). After the mixture was stirred at room temperature for 3 hours, copper (I) bromide-dimethylsulfide complex (225 mg, 1.1 mmol) was added to the mixture to prepare an organocopper reagent. After stirring for 10 minutes, 1,2-dichlorobenzene solution (10 mL) of $C_{60}$ (36 mL, 0.05 mmol) was added thereto at once. After stirring for 2 hours, the reaction was terminated by the addition of saturated ammonium chloride solution (0.05 mL). The reaction mixture was diluted with toluene (10 mL), and copper salt was removed by a silica gel column. The obtained filtrate was concentrated and purified by preparative GPC to obtain Compound 13 (78 mg, isolated yield: 87%). Note that "Bu" represents butyl in the present specification.

NMR data of the obtained Compound 13 were as follows.

$^1$H NMR (CDCl$_3$) δ 0.21 (s 6H, SiMe$_2$) 0.24 (s, 12H, 2SiMe$_2$), 0.6 (s, 12H, 2SiMe$_2$), 0.73) (m, 10H, 5SiCH$_2$). 0.93 (m, 15H, 5CH$_2$CH$_3$), 1.40 (m, 20H, 10CH$_2$), 5.22 (s, 1H, C$_{60}$H), 7.28 (s, 4H, ArH), 7.32 (d, J=8.55 Hz, 4H, ArH), 7.46 (d, J=8.55 Hz, 4H, ArH), 7.48 (d, J=8.55 Hz, 4H, ArH), 7.68 (d, J=8.55 Hz, 4H, ArH). $^{13}$C(CDCl$_3$): δ −1.73 (6C, 3SiMe$_2$), 1.01 (4C, 2SiMe$_2$), 13.84 (5C, 5SiCH$_2$), 15.84 (3C, 3Cl$_2$CH$_3$), 15.86 (2C, 2CH$_2$CH$_3$), 26.02 (5C, 5CH$_2$), 26.25 (3C, 3CH$_2$), 26.27 (2C, 2CH$_2$), 58.60 (2C, 2C$_{60}$(C$_α$)), 58.72 (1C, C$_{60}$(C$_α$)), 60.73 (2C, 2C$_{60}$(C$_α$)), 62.87 (1C, C$_{60}$(CH)), 94.74 (2C, 2C≡CSi), 94.77 (1C, C≡CSi), 94.94 (2C, 2C≡CSi), 104.56 (1C, C≡CSi), 104.78 (2C, 2C≡CSi), 104.86 (2C, 2C≡CSi), 122.45 (1C, Ar), 122.70 (2C, Ar), 122.97 (2C, Ar), 127.34 (2C, Ar), 127.64 (4C, Ar), 127.66 (4C, Ar), 132.42 (4C, Ar), 132.55 (2C, Ar), 132.65 (4C, Ar), 139.55, 139.57, 143.24, 143.43, 144.11, 144.23, 144.30, 144.41, 145.13, 145.38, 145.47, 145.61, 145.67, 146.89, 147.07, 147.16, 147.27, 147.74, 148.10, 148.14, 148.25, 148.38, 148.67, 148.77, 148.80, 150.90, 151.81, 152.46, 155.54.

Compound 13 was orange powder at room temperature. The compound in the solid state was stable in air at room temperature.

By slowly diffusing ethanol in toluene solution of Compound 13, orange single crystal suitable for X-ray crystal structure analysis was obtained. Crystallographic data of crystal of Compound 13 were as follows:

Crystalline System: Monoclinic, Space Group: P 21/n

| a, Å | 18.564 |
|---|---|
| b, Å | 17.636 |
| c, Å | 32.451 |
| α, deg | 90.000 |
| β, deg | 99.671 |
| γ, deg | 90.000 |
| Volume V, Å3 | 10473(4) |
| Number of molecules in unit cell Z, | 4 |
| Temperature, K | 153(2) |
| Crystal size, mm | 0.75 × 0.45 × 0.20 |
| Number of independent reflections | 17181 |
| Number of parameters | 1107 |
| R1, wR2 (all data) | 0.2769, 0.5134 |
| R, Rw (I > 2.0s(I)) | 0.1877, 0.4567 |
| GOF on F2 | 1.701 |

Figure 6:
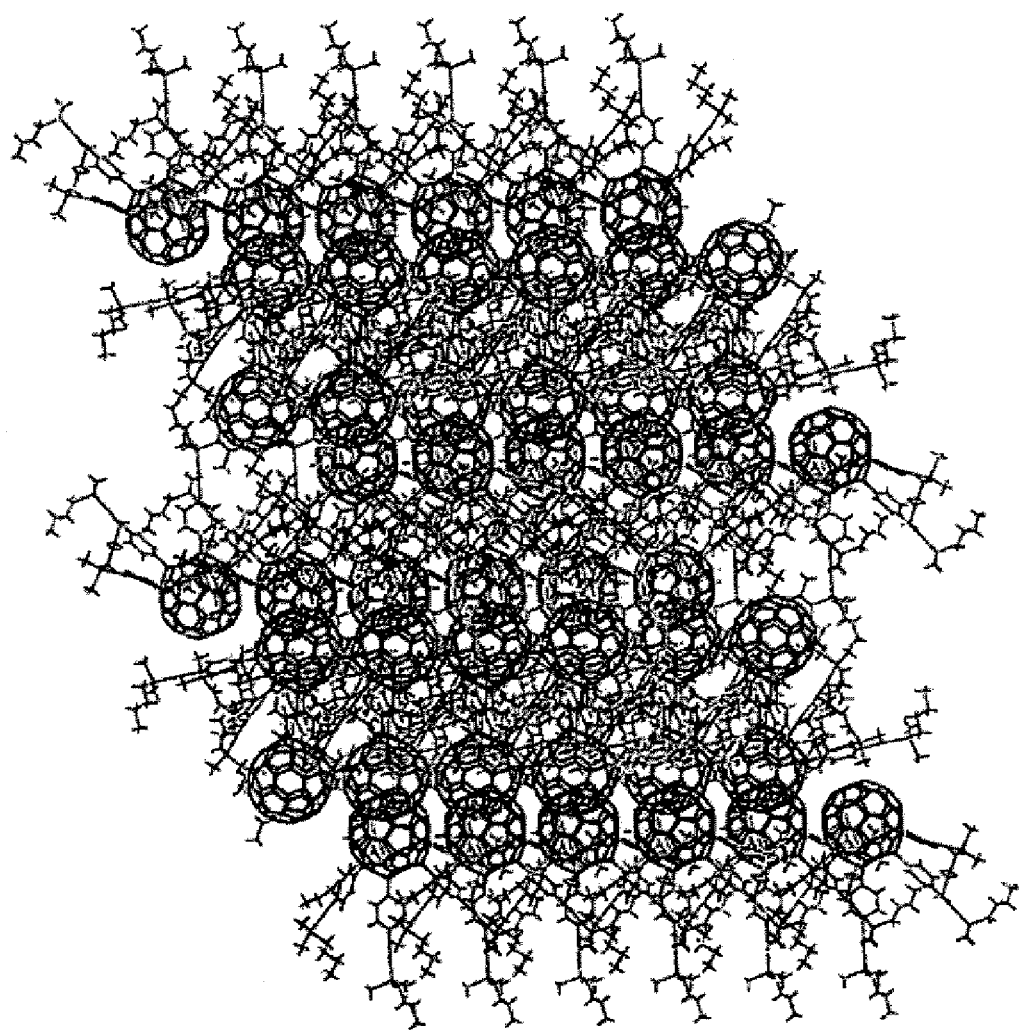
FIG. 6 shows the structure of Compound 13.

When crystal of Compound 13 was subjected to X-ray structure analysis, the structure was as shown in FIG. 6.

Example 7

Compound Represented by the Following Formula (14)

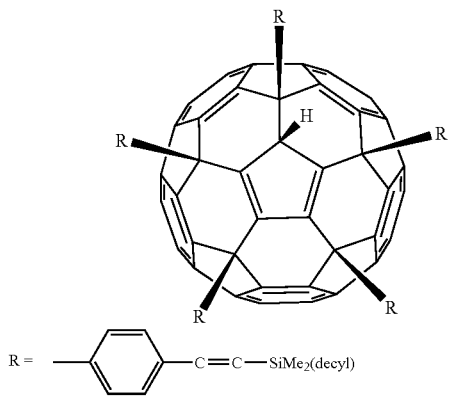

(14)

$R = $ <image of phenyl group> $C≡C-SiMe_2(decyl)$ i-propylmagnesiumbromide (0.67 M/THF solution, 3.10 mL, 2.1 mmol) was added dropwise to THF solution (15 mL) of 1-bromo-4-ethynylbenzene (382 mg, 2.0 mmol) at 0° C. After the mixture was stirred for 20 minutes, an ice water bath was removed. After stirring at room temperature for 10 minutes, n-decyldimethylsilyl chloride (1.5 mL, 4.0 mmol) was added to the mixture. After stirring for 2 hours, the reaction was terminated by the addition of saturated ammonium chloride solution (5 mL). The reaction mixture was extracted with ethyl acetate, and it was concentrated and thereafter purified by means of flash column chromatography to obtain colorless liquid, (4-decylphenylethynyl)-n-butyldimethylsilane (646 mg, isolated yield: 85%).

THF solution (4 mL) of (4-decylphenylethynyl)-n-butyldimethylsilane obtained (529 mg, 1.3 mmol) was added dropwise to THF suspension (2 mL) of magnesium turnings (32 mg, 1.3 mmol). After the mixture was stirred at room temperature for 3 hours, copper (I) bromide-dimethylsulfide complex (287 mg, 1.4 mmol) was added to the mixture to prepare an organocopper reagent. After stirring for 10 minutes, 1,2-dichlorobenzene solution (10 mL) of $C_{60}$ (50 mL, 0.07 mmol) was added thereto at once. After stirring for 2 hours, the reaction was terminated by the addition of saturated ammonium chloride solution (0.05 mL). The reaction mixture was diluted with toluene (10 mL), and copper salt was removed by a silica gel column. The obtained filtrate was concentrated and purified by preparative GPC to obtain Compound 14 (153 mg, isolated yield: 93%).

NMR data of the obtained Compound 14 were as follows:

$^1$H NMR (CDCl$_3$): δ 0.21 (s, 6H, SiMe$_2$), 0.24 (s, 12H, 2SiMe$_2$), 0.26 (s, 12H, 2SiMe$_2$), 0.73 (m, 10H, 5SiCH$_2$), 0.86 (m, 15H, 5CH$_2$CH$_3$), 1.20-1.50 (m, 100H, 50CH$_2$), 5.22 (s, 1H, C$_{60}$H), 7.29 (s, 4H, ArH), 7.31 (d, J=8.00 Hz, 4H, ArH), 7.45 (d, J=8.00 Hz, 4H, ArH), 7.49 (d, J=8.00 Hz, 4H, ArH), 7.68 (d, J=8.00 Hz, 4H, ArH), $^{13}$C NMR (CDCl$_3$): δ −1.72 (10C, 5SiMe$_2$), 14.13 (5C, 5SiCH$_2$), 16.09 (5C, 5CH$_2$CH$_3$), 22.69 (5C, 5CH$_2$), 23.78 (5C, 5CH$_2$), 29.32 (m, 10C, 10CH$_2$), 29.66 (m, 20C, 20CH$_2$), 31.91 (5C, 5CH$_2$), 33.29 (5C, 5CH$_2$), 58.60 (2C, 2C$_{60}$(C$_{60}$)), 58.72 (1C, C$_\alpha$)), 60.73 (2C, temperature for 3 hours, copper (I) bromide-dimethylsulfide complex (287 mg, 1.4 mmol) was added to the mixture to prepare an organocopper reagent. After stirring for 10 minutes, 1,2-dichlorobenzene solution (10 mL) of C$_{60}$ (50 ml, 0.07 mmol) was added thereto at once. After stirring for 2 hours, the reaction was terminated by the addition of saturated ammonium chloride solution (0.05 mL). The reaction mixture was diluted with toluene (10 mL), and copper salt was removed by a silica gel column. The obtained filtrate was concentrated and purified by preparative GPC to obtain Compound 15 (133 mg, isolated yield: 86%).

NMR data of the obtained Compound 15 were as follows:

$^1$H NMR (CDCl$_3$): δ 0.22 (s, 6H, SiMe$_2$), 0.25 (s, 12H, 2SiMe$_2$), 0.27 (s, 12H, 2SiMe$_2$), 0.73 (m, 10H1, 5SiCH$_2$), 0.85 (m, 15H, 5CH$_2$CH$_3$), 1.26-1.56 (m, 80H, 40CH$_2$), 5.22 (s, 1H, C$_{60}$H), 7.29 (s, 4H, ArH), 7.32 (d, J=8.00 Hz, 4H, ArH), 7.45 (d, J=8.00 Hz, 4H, ArH), 7.49 (d, J=8.00 Hz, 4H, ArH), 7.68 (d, J=8.00 Hz, 4H, ArH). $^{13}$C NMR (CDCl$_3$): δ −1.74 (4C, 2SiMe$_2$), −1.73 (4C, 2SiMe$_2$), −1.71 (2C, SiMe$_2$), 14.13 (5C, 5SiCH$_2$), 16.08 (1C, CH$_2$CH$_3$), 16.12 (4C, 4CH$_2$CH$_3$), 22.69 (5C, 5CH$_2$), 23.76 (3C, 3CH$_2$), 23.79 (2C, 2CH$_2$), 29.32 (m, 10C, 10CH$_2$), 29.66 (m, 1C, 10CH$_2$), 31.90 (5C, 5CH$_2$), 33.29 (5C, 5CH$_2$), 58.58 (2C, 2C60(Cα)), 58.71 (1C, C60(Cα)), 60.72 (2C, 2C60(Cα)), 62.85 (1C, C60 (CH)), 94.75 (2C, 2C≡CSi), 94.77 (1C, C≡CSi), 94.96 (2C, 2C≡CSi), 104.55 (1C, C≡CSi), 104.76 (2C, 2C≡CSi), 104.84 (2C, 2C≡CSi), 122.45 (1C, Ar), 122.70 (2C, Ar), 122.97 (2C, Ar), 127.31 (2C, Ar), 127.60 (4C, Ar), 127.63 (4C, Ar), 132.42 (4C, Ar), 132.54 (2C, Ar), 132.65 (4C, Ar), 139.54, 139.56, 143.23, 143.42, 144.10, 144.22, 144.23, 144.30, 144.40, 145.12, 145.36, 145.47, 145.60, 145.67, 146.88, 147.07, 147.15, 147.26, 147.74, 148.09, 148.14, 148.24, 148.38, 148.66, 148.77, 148.80, 150.90, 151.81, 152.46, 155.52.

Compound 15 was orange solid with high viscosity at room temperature. Further, the compound in the solid state was stable in air at room temperature.

Figure 8:
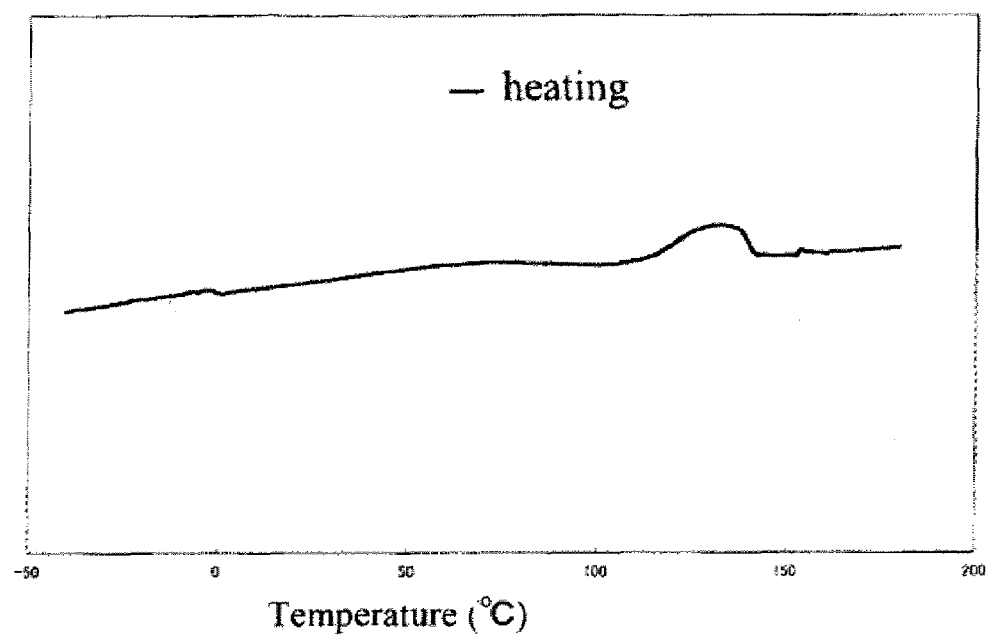
FIG. 8 shows DSC measurement result of Compound 15.

Compound 15 was subjected to DSC measurement, and measurement results were as shown in FIG. 8.

It was confirmed from FIG. 8 that the derivative of Compound 15 exhibits an intermediate phase at a temperature of 131° C. or lower.

INDUSTRIAL APPLICABILITY

The fullerene derivative obtained in the present invention has an ordered 2C$_{60}$(C$_\alpha$)), 62.86 (1C, C$_{60}$(CH)), 94.75 (2C, 2C≡CSi), 94.96 (3C, 3C≡CSi), 104.54 (1C, C≡CSi), 104.75 (2C, 2C≡CSi), 104.83 (2C, 2C≡CSi), 122.46 (1C, Ar), 122.71 (2C, Ar), 122.98 (2C, Ar), 127.32 (2C, Ar), 127.61 (4C, Ar), 127.63 (4C, Ar), 132.43 (4C, Ar), 132.54 (2C, Ar), 132.65 (4C, Ar), 139.56, 143.25, 143.43, 144.11, 144.22, 144.24, 144.30, 144.25, 144.30, 144.41, 145.13, 145.36, 145.47, 145.61, 145.69, 146.89, 147.09, 147.17, 147.28, 147.75, 148.11, 148.16, 148.26, 148.40, 148.68, 148.79, 148.82, 150.91, 151.83, 152.48, 155.54.

Compound 14 was orange solid with high viscosity at room temperature. The compound in the solid state was stable in air at room temperature.

Figure 7:
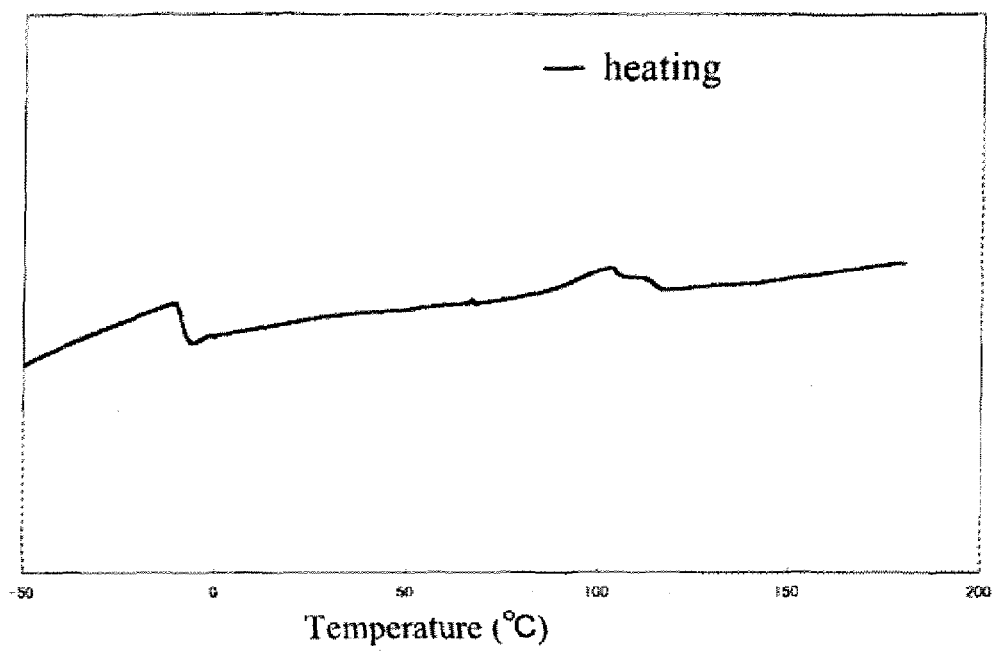
FIG. 7 shows DSC measurement result of Compound 14.

Compound 14 was subjected to DSC measurement, and measurement results were as shown in FIG. 7.

It was confirmed from FIG. 7 that the derivative of Compound 14 has phase transition at 102° C. and 110° C. and exhibits an intermediate phase at a temperature of 110° C. or lower.

Example 8

Compound Represented by the Following Formula (15)

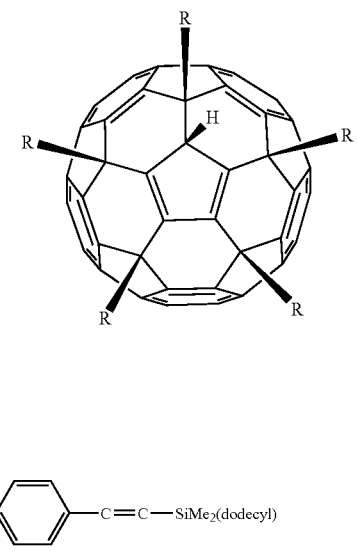

(15)

R = —⟨benzene⟩—C≡C—SiMe$_2$(dodecyl)

i-propylmagnesiumbromide (0.67 M/TH solution, 3.10 mL, 3.1 mmol) was added dropwise to THF solution (15 mL) of 1-bromo-4-ethynylbenzene (382 mg, 2.0 mmol) at 0° C. After the mixture was stirred for 20 minutes, an ice water bath was removed. After stirring at room temperature for 10 minutes, n-dodecyldimethylsilyl chloride (1.5 mL, 4.0 mmol) was added to the mixture. After stirring for 2 hours, the reaction was terminated by the addition of saturated ammonium chloride solution (5 mL). The reaction mixture was extracted with ethyl acetate, and it was concentrated and thereafter purified by means of flash column chromatography to obtain colorless liquid, (4-dodecylphenylethynyl)-n-butyldimethylsilane (627 mg, isolated yield: 77%).

THF solution (4 mL) of (4-dodecyl phenylethynyl)-n-butyldimethylsilane obtained (492 mg, 1.3 mmol) was added dropwise to THF suspension (2 mL) of magnesium turnings (32 mg, 1.3 mmol). After the mixture was stirred at room structure with high regularity, in which, for example, the fullerene derivative has a layer crystalline structure in which no organic group is positioned between fullerene skeletons. Temperature of transition to an isotropic phase of the structure is higher and stabler compared to that of a columnar structure, and therefore the fullerene derivative of the present invention is useful as a liquid crystal material. Moreover, the fullerene derivative obtained in the present invention is stable, for example, in air, and therefore can be used as an electron-conductive material and an optical functional material.

The invention claimed is:

1. A fullerene derivative represented by the following formula (1):

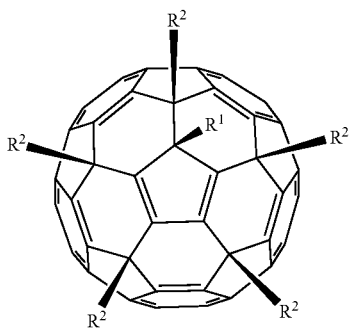

(1)

wherein:
R$^1$ is a substituted or unsubstituted organic group or a hydrogen atom; and
each R$^2$ is independently a group represented by the following formula (3) or (4),

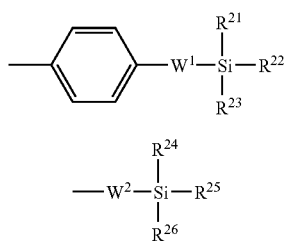

wherein:
W$^1$ is C$_2$-C$_{12}$ alkynylene, wherein any —CH$_2$— in the alkynylene is optionally substituted with —O—, —S—, —C(=O)O—, or —O—C(=O)—;
W$^2$ is a single bond, C$_1$-C$_{11}$ alkylene, C$_2$-C$_{12}$ alkenylene, or C$_2$-C$_{12}$ alkynylene, wherein any —CH$_2$— in the alkylene, alkenylene or alkynylene is optionally substituted with —O—, —S—, —C(=O)O—, or —O—C(=O)—;
R$^{21}$ to R$^{25}$ are each independently a substituted or unsubstituted C$_1$-C$_{20}$ alkyl group, a substituted or unsubstituted C$_2$-C$_{15}$ alkenyl group, or a substituted or unsubstituted C$_2$-C$_{15}$ alkynyl group; and
R$^{26}$ is a substituted or unsubstituted C$_4$-C$_{20}$ alkyl group, a substituted or unsubstituted C$_4$-C$_{15}$ alkenyl group, or a substituted or unsubstituted C$_4$-C$_{15}$ alkynyl group,
wherein the fullerene derivative in the crystal state or the liquid crystal state has a layer structure.

2. The fullerene derivative according to claim 1, wherein R$^1$ is a substituted or unsubstituted C$_1$-C$_{20}$ hydrocarbon group, a substituted or unsubstituted C$_1$-C$_{20}$ alkoxy group, a substituted or unsubstituted C$_6$-C$_{20}$ aryloxy group, a substituted or unsubstituted amino group, a substituted or unsubstituted silyl group, a substituted or unsubstituted alkylthio group (—SY$^1$: in the formula, Y$^1$ is a substituted or unsubstituted C$_1$-C$_{20}$ alkyl group), a substituted or unsubstituted arylthio group (—SY$^2$: in the formula, Y$^2$ is a substituted or unsubstituted C$_6$-C$_{18}$ aryl group), a substituted or unsubstituted alkylsulfonyl group (—SO$_2$Y$^3$: in the formula, Y$^3$ is a substituted or unsubstituted C$_1$-C$_{20}$ alkyl group), or a substituted or unsubstituted arylsulfonyl group (—SO$_2$Y$^4$: in the formula, Y$^4$ is a substituted or unsubstituted C$_6$-C$_{18}$ aryl group).

3. The fullerene derivative according to claim 1, wherein R$^1$ is a substituted or unsubstituted C$_1$-C$_{10}$ alkyl group, a substituted or unsubstituted C$_1$-C$_{10}$ alkenyl group, or a substituted or unsubstituted C$_1$-C$_{10}$ alkynyl group.

4. The fullerene derivative according to claim 1, wherein R$^1$ has one or more substituents selected from the group consisting of ester group, carboxyl group, amide group, alkyne group, trimethylsilyl group, trimethylsilylethynyl group, aryl group, amino group, phosphonyl group, thio group, carbonyl group, nitro group, sulfo group, imino group, halogeno group, and alkoxy group.

5. The fullerene derivative according to claim 1, wherein W$^1$ is —C≡C—.

6. The fullerene derivative according to claim 1, wherein W$^2$ is a single bond, C$_1$-C$_4$ alkylene, C$_2$-C$_4$ alkenylene, or C$_2$-C$_4$ alkynylene.

7. The fullerene derivative according to claim 1, wherein R$^{21}$, R$^{22}$, R$^{24}$ and R$^{25}$ are methyl groups.

8. The fullerene derivative according to claim 1, which has an intermediate phase.

9. A composition, which comprises the fullerene derivative according to claim 1, and which has an intermediate phase.

* * * * *